US010557153B2

(12) United States Patent
De Laat et al.

(10) Patent No.: US 10,557,153 B2
(45) Date of Patent: Feb. 11, 2020

(54) DEGRADATION OF LIGNOCELLULOSIC MATERIAL

(75) Inventors: Wilhelmus Theodorus Antonius Maria De Laat, Echt (NL); Manoj Kumar, Echt (NL); Margot Elisabeth Francoise Schooneveld-Bergmans, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 620 days.

(21) Appl. No.: 13/057,598

(22) PCT Filed: Aug. 4, 2009

(86) PCT No.: PCT/EP2009/060098
§ 371 (c)(1),
(2), (4) Date: Feb. 4, 2011

(87) PCT Pub. No.: WO2010/018105
PCT Pub. Date: Feb. 18, 2010

(65) Prior Publication Data
US 2011/0143402 A1 Jun. 16, 2011

(30) Foreign Application Priority Data

Aug. 11, 2008 (EP) .................................. 08162154

(51) Int. Cl.
C12P 7/10 (2006.01)
C12P 19/02 (2006.01)
C12P 19/14 (2006.01)
C13K 1/02 (2006.01)

(52) U.S. Cl.
CPC ...................................... *C12P 7/10* (2013.01)

(58) Field of Classification Search
USPC ............................ 435/155, 69.1, 165; 426/48
See application file for complete search history.

(56) References Cited

U.S. PATENT DOCUMENTS

| 8,202,709 | B2 * | 6/2012 | Tolan et al. ...................... 435/99 |
| 2005/0257905 | A1 * | 11/2005 | Shoseyov ........................ 162/72 |
| 2007/0128690 | A1 * | 6/2007 | Foreman et al. ............ 435/69.1 |
| 2008/0138862 | A1 | 6/2008 | Felby et al. |
| 2008/0145903 | A1 * | 6/2008 | Holmes et al. ................ 435/155 |
| 2008/0182323 | A1 * | 7/2008 | Felby et al. ................... 435/274 |
| 2009/0004714 | A1 | 1/2009 | Norholm et al. |
| 2009/0258404 | A1 * | 10/2009 | Mikkelsen et al. ............ 435/139 |
| 2010/0028485 | A1 | 2/2010 | Tuohy et al. |
| 2010/0203593 | A1 | 8/2010 | Foreman et al. |
| 2010/0291650 | A1 * | 11/2010 | Larsen et al. ................. 435/165 |

FOREIGN PATENT DOCUMENTS

| WO | 2006/056838 A1 | 6/2006 |
| WO | 2007/036795 A1 | 4/2007 |
| WO | 2007/091231 A9 | 8/2007 |
| WO | WO 2007/091231 | * 8/2007 |
| WO | WO2007091231 | * 8/2007 |
| WO | 2008/023060 A1 | 2/2008 |
| WO | 2009/026722 A1 | 3/2009 |

OTHER PUBLICATIONS

Foong et al., Unravelling the mysteries of the Cellulosome, Australasian Biotechnology, vol. 7, No. 4, pp. 310-314, Oct. 1997.*
Perez et al., Biodegradation and biological treatments of cellulose, hemicellulose and lignin, Int. Microbiol. 5:53-63, 2002.*
Murray et al., Isolation and characterization of a thermostable endo-b-glucanase active on 1,3-1,4-b-D-glucans from the aerobic fungus *Talaromyces emersonii* CBS 814.70, Enzyme and Microbial Technology 29 (2001) 90-98.*
Viikari et al., Thermostable Enzymes in Lignocellulose Hydrolysis, Adv Biochem Engin/Biotechnol (2007) 108: 121-145.*
Ren, PhD Thesis, Effect of Cell Wall Degrading Enzymes and Chemicals on Corn Stover Preservation and Pretreatment During Ensilage Processing, 2006.*
International Search Report for PCT/EP2009/060098, dated Jan. 7, 2010.
Saloheimo, M. et al., "Swollenin, a Trichoderma reesei protein with sequence similarity to the plant expansins, exhibits disrupt activity on cellulosic materials", European Journal of Biochemistry, vol. 269, No. 17, (Sep. 1, 2002), pp. 4202-4211.
Larsen, J. et al., "The IBUS Process—Lignocellulosic Bioethanol Close to a Commercial Reality", Chemical Engineering & Technology, vol. 21, No. 5, (Apr. 22, 2008), pp. 765-772.
Hodge et al., "Soluble and insoluble solids contributions to high-solids enzymatic hydrolysis of lignocellulose." Bioresource Technology 99 (2008) 8940-8948.
Kristensen et al., "Yield-determining factors in high-solids enzymatic hydrolysis of lignocellulose." Biotechnology for Biofuels 2:11 (2009).
Varga et al., "High Solid Simultaneous Saccharification and Fermentation of Wet Oxidized Corn Stover to Ethanol." Biotechnology and Bioengineering 88:05 (2004).
Grassick, Alice et al., "Three-Dimensional Structure of a Thermostable Native Cellobiohydrolase, CBH IB, and Molecular Characterization of the CEL7 Gene From the Filamentous Fungus, Talaromyces Emersonii", European Journal of Biochemistry, 2004, pp. 4495-4506, vol. 271.
McHale, Anthony et al., "The Cellulolytic System of Talaromyces Emersonii: Purification and Characterization of the Extracellular and Intracellular β-Glucosidases", Biochimica et Biophysica Acta, 1981, pp. 152-159, vol. 662.
Murray, Patrick et al., "Isolation and Characterization of a Thermostable Endo-β-Glucanase Active on 1,3-1,4-β-D-Glucans From the Aerobic Fungus *Talaromyces emersonii* CBS 814.70", Enzyme and Microbial Technology, 2001, pp. 90-98, vol. 29.

(Continued)

*Primary Examiner* — Louise W Humphrey
*Assistant Examiner* — Srikanth Patury
(74) *Attorney, Agent, or Firm* — McBee Moore & Vanik IP, LLC

(57) ABSTRACT

The present invention describes a method for the treatment of lignocellulosic material which method comprises contacting said lignocellulosic material with a composition comprising two or more enzyme activities, said enzyme activities being cellulase and/or hemicellulase activities, wherein the pH during the treatment is about 4.5 or lower, and the treatment is carried out at a dry matter content of 15% or more.

19 Claims, 10 Drawing Sheets

(56) References Cited

OTHER PUBLICATIONS

Murray, P.G. et al., "Molecular Cloning, Transcriptional, and Expression Analysis of the First Cellulase Gene (CBH2), Encoding Cellobiohydrolase II, From the Moderately Thermo Philic Fungus *Talaromyces emersonii* and Structure Prediction of the Gene Product", Biochemical and Biophysical Research Communications, 2003, pp. 280-286, vol. 301.

Murray, Patrick et al., "Expression in Trichoderma Reesei and Characterisation of a Thermostable Family 3 β-Glucosidase From the Moderately Thermophilic Fungus *Talaromyces emersonii*", Protein Expression and Purification, 2004, pp. 248-257, vol. 38.

Tuohy, Maria G. et al., "Kinetic Parameters and Mode of Action of the Cellobiohydrolases Produced by Talaromyces Emersonii", Biochimica et Biophysica Acta, 2002, pp. 366-380, vol. 1596.

Jorgensen, Henning et al., "Liquefaction of Lignocellulose at High-Solids Concentration", Biotechnology and Bioengineering, Apr. 1, 2007, vol. 96, No. 5.

Karboune, Salwa et al., "Characterization of Selected Cellulolytic Activities of Multi-enzymatic Complex System from Penicillium funiculosum", Journal of Agricultural and Food Chemistry, 2008, pp. 903-909, vol. 56, No. 3.

Picart, P. et al., "Cellulases from two *Penicillium* sp. strains isolated from subtropical forest soil: production and characterization", Letters in Applied Microbiology, 2007, pp. 108-113, vol. 45.

Rao, Mala et al., "Effect of Pretreatment on the Hydrolysis of Cellulose by Penicillium Funiculosum Cellulase and Recovery of Enzyme", Biotechnology and Bioengineering, 1983, pp. 1863-1871, vol. 25.

\* cited by examiner

DEGRADATION OF LIGNOCELLULOSIC MATERIAL

This application is the U.S. national phase of International Application No. PCT/EP2009/060098 filed 4 Aug. 2009, which designated the U.S. and claims priority to EP Application No. 08162154.2 filed 11 Aug. 2008, the entire contents of each of which are hereby incorporated by reference.

FIELD OF THE INVENTION

The invention relates to methods for degrading lignocellulosic material and to methods for producing a sugar or sugars from such material. The invention also relates to methods for producing a fermentation product.

BACKGROUND OF THE INVENTION

Carbohydrates constitute the most abundant organic compounds on earth. However, much of this carbohydrate is sequestered in complex polymers including starch (the principle storage carbohydrate in seeds and grain), and a collection of carbohydrates and lignin known as lignocellulose. The main carbohydrate components of lignocellulose are cellulose, hemicellulose, and pectins. These complex polymers are often referred to collectively as lignocellulose.

Bioconversion of renewable lignocellulosic biomass to a fermentable sugar that is subsequently fermented to produce alcohol (e.g., ethanol) as an alternative to liquid fuels has attracted an intensive attention of researchers since 1970s, when the oil crisis broke out because of decreasing the output of petroleum by OPEC. Ethanol has been widely used as a 10% blend to gasoline in the USA or as a neat fuel for vehicles in Brazil in the last two decades. More recently, the use of E85, an 85% ethanol blend has been implemented especially for clean city applications. The importance of fuel bioethanol will increase in parallel with increases in prices for oil and the gradual depletion of its sources. Additionally, fermentable sugars are being used to produce plastics, polymers and other biobased products and this industry is expected to grow substantially therefore increasing the demand for abundant low cost fermentable sugars which can be used as a feed stock in lieu of petroleum based feedstocks.

The sequestration of such large amounts of carbohydrates in plant biomass provides a plentiful source of potential energy in the form of sugars, both five carbon and six carbon sugars that could be utilized for numerous industrial and agricultural processes. However, the enormous energy potential of these carbohydrates is currently under-utilized because the sugars are locked in complex polymers, and hence are not readily accessible for fermentation. Methods that generate sugars from plant biomass would provide plentiful, economically-competitive feedstocks for fermentation into chemicals, plastics, and fuels.

Regardless of the type of cellulosic feedstock, the cost and hydrolytic efficiency of enzymes are major factors that restrict the commercialization of the biomass bioconversion processes. The production costs of microbially produced enzymes are tightly connected with a productivity of the enzyme-producing strain and the final activity yield in the fermentation broth.

In spite of the continued research of the last few decades to understand enzymatic lignocellulosic biomass degradation and cellulase production, it remains desirable to discover or to engineer new highly active cellulases and hemicellulases. It would also be highly desirable to construct highly efficient enzyme compositions capable of performing rapid and efficient biodegradation of lignocellulosic materials.

In addition, currently available enzymes having cellulase activity, typically derived from *Trichoderma*, function at mesophilic temperatures, such as from 45° C. to 50° C. and at pH 5.0. This, however, may lead to bacterial infection reducing product yield, so it is desirable to carry out saccharification at a temperature of 65° C. or higher. In addition, the use of mesophilic temperatures increases the viscosity of the biomass being used such that the dry matter content used is limited. Also, when acid pretreated biomass is used as a substrate, the pH must be raised so that the enzyme can saccharify the sugars in the biomass. In the context of a commercially viable fuel ethanol industry, this implies a requirement for, for example, sodium hydroxide or calcium sulphate and the production of huge quantities of the corresponding salts, for example gypsum in the case of sodium hydroxide. Accordingly, it is desirable to carry out saccharification using an enzyme which can operate at a pH of pH 4.0 or lower.

SUMMARY OF THE INVENTION

We have shown that an enzyme preparation derived from *Talaromyces emersonii* can extremely effectively hydrolyze lignocellulolytic material, for example corn stover or wheat straw, into monomeric sugars which can then be converted into a useful product, such as ethanol. The enzyme preparation comprises cellulase and hemicellulase activities.

Surprisingly, this invention now shows that the said enzyme preparation can be used to carry out highly effective hydrolysis of a lignocellulosic substrate (achieving in excess of 90% conversion of cellulose). The preparation has a higher specific activity than other products available in the market. This is highly significant in the context of commercially viable fuel ethanol production from lignocellulosic biomass since lower amounts of enzyme will be required (as compared with currently available products).

Moreover, this hydrolysis may be carried out at a high temperature which (i) reduces the risk of bacterial infection and (ii) results in a less viscous biomass pulp. The effect of the latter is significant since it enables the better blending of enzymes, resulting in a higher operational dry matter in the plant and allows a consequent higher ethanol concentration to be achieved. Thus, less energy need be used improving sustainability and a smaller fermentation process will be required requiring lower investment.

Also, this hydrolysis may be carried out at low pH. This is desirable since biomass is often pretreated with acid. Biomass treated in this way does not have to be pH adjusted if the enzymes subsequently used for saccharification are capable of acting at low pH. This implies a lower requirement of, for example, sodium hydroxide or calcium sulphate and a process in which there is no waste salt. This is significant in a process in which, for example, fuel ethanol is to be produced since huge quantities of material are consumed in such processes. This allows a process to be carried out in which no pH adjustment is required, i.e. there is no requirement for the addition of acids or bases. The process may thus be carried out as a zero waste process and/or as a process in which no inorganic chemical input is required.

In addition, it has been shown that the enzyme composition can effectively hydrolyze biomass when high dry matter contents are used. It is highly desirable that enzymes used in the production of, for example, fuel ethanol are able to operate on substrates having high viscosity (i.e. high dry weight composition) since this allows higher amounts of the final product, for example, fuel ethanol, to be achieved.

According to the invention, there is thus provided a method for the treatment of lignocellulosic material which method comprises contacting said lignocellulosic material with a composition comprising two or more enzyme activities, said enzyme activities being cellulase and/or hemicellulase activities, wherein the pH during the treatment is about 4.5 or lower, and the treatment is carried out at a dry matter content of 15% or more.

The invention also provides:
method for producing a sugar or sugars from lignocellulosic material which method comprises contacting said lignocellulosic material with a composition as defined above;
a method for producing a fermentation product, which method comprises:
producing a fermentable sugar using a method as set out above; and
fermenting the resulting fermentable sugar, thereby to produce a fermentation product;
use of a composition as defined above in the treatment of lignocellulosic material; and
use of a composition as defined above in the production of a sugar or sugars from lignocellulosic material.

BRIEF DESCRIPTION OF THE DRAWINGS

FIG. 1 shows glucose formation from dilute acid pretreated corn stover using different enzyme dosages at 50° C., pH 4.5-5.

FIGS. 2 and 3 show specific activity data for sugar formation from dilute acid pretreated corn stover.

DETAILED DESCRIPTION OF THE INVENTION

Figure 1A:
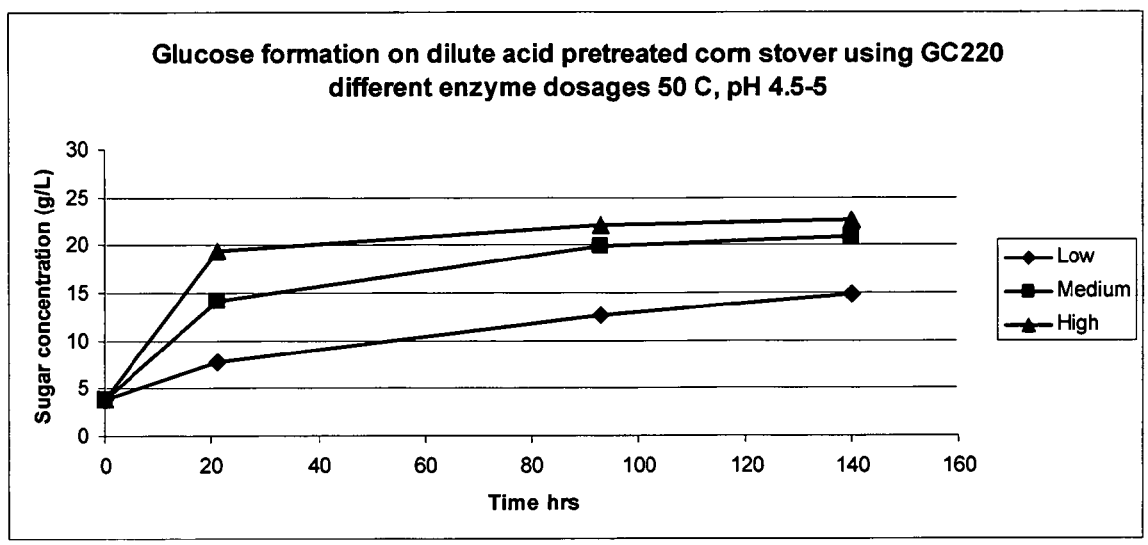
FIG. 1a=GC 220.

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The present invention provides relates to a composition which comprises cellulolytic and/or hemicellulolytic enzyme activity and which has the ability to modify, for example degrade, a non-starch carbohydrate material. A non-starch carbohydrate material is a material which comprises, consists of or substantially consists of one or more non-starch carbohydrates. Carbohydrate in this context includes all saccharides, for example polysaccharides, oligosaccharides, disaccharides or monosaccharides.

A composition as described herein typically modifies a non-starch carbohydrate material by chemically modification of such material. Chemical modification of the carbohydrate material may result in the degradation of such material, for example by hydrolysis, oxidation or other chemical modification such as by the action of a lyase.

A non-starch carbohydrate suitable for modification by a composition as described herein is lignocellulose. The major polysaccharides comprising different lignocellulosic residues, which may be considered as a potential renewable feedstock, are cellulose (glucans), hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to interstrand hydrogen bonding than the highly branched α-linked structures of starch. Thus, cellulose polymers are generally less soluble, and form more tightly bound fibers than the fibers found in starch.

Endoglucanases (EG) and exo-cellobiohydrolases (CBH) catalyze the hydrolysis of insoluble cellulose to cellooligosaccharides (cellobiose as a main product), while β-glucosidases (BG) convert the oligosaccharides, mainly cellobiose and cellotriose to glucose.

Hemicellulose is a complex polymer, and its composition often varies widely from organism to organism, and from one tissue type to another. In general, a main component of hemicellulose is β-1,4-linked xylose, a five carbon sugar. However, this xylose is often branched at 0-3 and/or 0-2 atom of xylose, and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Xylanases together with other accessory enzymes, for example α-L-arabinofuranosidases, feruloyl and acetylxylan esterases, glucuronidases, and β-xylosidases) catalyze the hydrolysis of hemicelluloses.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another.

The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

A composition for use in a method of the invention will comprise enzymatic activities typically derived from a saprophyte fungal microorganism of the class *Penicillium* and from the genus *Talaromyces*, for example *Talaromyces emersonii*. *Talaromyces emersonii* may also be referred to as *Geosmithia emersonii* or *Penicillium emersonii*. *Talaromyces emersonii* has also been referred to as *Talaromyces duponti* and *Penicillium duponti*.

A composition for use in a method of the invention comprises at least two activities, although typically a composition will comprise more than two activities, for example, three, four, five, six, seven, eight, nine or more. Typically, a composition of the invention may comprise at least one cellulase and at least one hemicellulase. However, a composition of the invention may comprise cellulases, but no xylanases. In addition, a composition of the invention may comprise auxiliary enzyme activity, i.e. additional activity which, either directly or indirectly leads to lignocellulose degradation. Examples of such auxiliary activities are mentioned herein.

Thus, a composition for use in the invention may comprise endoglucanase activity and/or cellobiohydrolase activity and/or R-glucosidase activity. A composition for use in the invention may comprise more than one enzyme activity in one or more of those classes. For example, a composition for use in the invention may comprise two endoglucanase activities, for example, endo-1,3(1,4)-β glucanase activity and endo-β-1,4-glucanase activity. Such a composition may also comprise one or more xylanase activities. Such a composition may comprise an auxiliary enzyme activity.

A composition for use in the invention may be derived from *Talaromyces emersonii*. In the invention, it is anticipated that a core set of (lignocellulose degrading) enzyme activities may be derived from *Talaromyces emersonii*. *Talaromyces emersonii* can provide a highly effective set of activities as demonstrated herein for the hydrolysis of lignocellulosic biomass. That activity can then be supplemented with additional enzyme activities from other sources. Such additional activities may be derived from classical sources and/or produced by a genetically modified organism.

The activities in a composition for use in the invention may be thermostable. Herein, this means that the activity has a temperature optimum of 40° C. or higher, for example about 50° C. or higher, such as about 60° C. or higher, for example about 70° C. or higher, such as about 75° C. or higher, for example about 80° C. or higher such as 85° C. or higher. Activities in a composition for use in the invention will typically not have the same temperature optima, but preferably will, nevertheless, be thermostable.

In addition, enzyme activities in a composition for use in the invention may be able to work at low pH. For the purposes of this invention, low pH indicates a pH of about 5.5 or lower, about 5 or lower, about 4.9 or lower, about 4.8 or lower, about 4.7 or lower, about 4,6 or lower, about 4.5 or lower, about 4.4 or lower, about 4.3 or lower, about 4.2 or lower, about 4.1 or lower, about 4.0 or lower about 3.9 or lower, or about 3.8 or lower, about 3.7 or lower, about 3.6 or lower, or about 3.5 or lower.

Activities in a composition for use in the invention may be defined by a combination of any of the above temperature optima and pH values.

The composition used in a method of the invention may comprise, in addition to the activities derived from *Talaromyces*, a cellulase (for example one derived from a source other than *Talaromyces*) and/or a hemicellulase (for example one derived from a source other than *Talaromyces*) and/or a pectinase.

A composition for use in the invention may comprise one, two or three classes of cellulase, for example one, two or all of an endoglucanase (EG), an exo-cellobiohydrolase (CBH) and a β-glucosidase (BG). A composition for use in the invention may comprise two or more of any of these classes of cellulase.

The β-glucosidase enzyme native to *Talaromyces* is known to be very active, Vmax value for the *Talaromyces* β-glucosidase Cel3a is 512 IU/mg which is considerably higher than the values reported for the β-glucosidases from the other fungal sources (P. Murray et al./Protein Expression and PuriWcation 38 (2004) 248-257) Despite the high activity of the β-glucosidase in the compositions according to the invention, and the high glucose levels achieved, no glucose inhibition occurs. This is advantageous since high activities and high glucose levels may be combined using the compositions according to the invention.

A composition of the invention may comprise an activity which has a different type of cellulase activity and/or hemicellulase activity and/or pectinase activity than that provided by the composition for use in a method of the invention. For example, a composition of the invention may comprise one type of cellulase and/or hemicellulase activity and/or pectinase activity provided by a composition as described herein and a second type of cellulase and/or hemicellulase activity and/or pectinase activity provided by an additional cellulose/hemicellulase/pectinase.

Herein, a cellulase is any polypeptide which is capable of degrading or modifying cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulase. Such degradation will typically take place by way of a hydrolysis reaction.

Herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers.

A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Accordingly, a composition of the invention may comprise any cellulase, for example, a cellobiohydrolase, an endo-β-1,4-glucanase, a β-glucosidase or a β-(1,3)(1,4)-glucanase.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3; 1,4)-beta-D-glucan 3 (4) glucanohydrolase; substrates include laminarin, lichenin and cereal beta-D-glucans.

A composition of the invention may comprise any hemicellulase, for example, an endoxylanase, a β-xylosidase, a α-L-arabinofuranosidase, an α-D-glucuronidase, an acetyl xylan esterase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an acetyl xylan esterase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

Herein, a feruloyl esterase (EC 3.1.1.73) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A composition of the invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also been known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: (1,4-α-D-galacturonide)$_n$+H$_2$O=(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

A composition of the invention will typically comprise at least one cellulase and/or at least one hemicellulase and/or at least one pectinase (one of which is a polypeptide according to the invention). A composition of the invention may comprise a cellobiohydrolase, an endoglucanase and/or a β-glucosidase. Such a composition may also comprise one or more hemicellulases and/or one or more pectinases.

In addition, one or more (for example two, three, four or all) of an amylase, a protease, a lipase, a ligninase, a hexosyltransferase, a glucuronidase or an expansin or a cellulose induced protein or a cellulose integrating protein or like protein may be present in a composition of the invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalyzing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition for use in the invention may comprise an expansin or expansin-like protein, such as a swollenin (see Salheimo et al., Eur. J. Biohem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition for use in the invention may a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition for use in a method of the invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition for use in a method of the invention may be composed of enzymes from (1) commercial suppliers; (2) cloned genes expressing enzymes; (3) complex broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover or wheat straw), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses feedstock (such as corn stover or wheat straw) to provide nutrition to an organism that produces an enzyme(s). In this manner, plants that produce the enzymes may themselves serve as a lignocellulosic feedstock and be added into lignocellulosic feedstock.

In the uses and methods described herein, the components of the compositions described above may be provided concomitantly (i.e. as a single composition per se) or separately or sequentially.

The invention thus relates to methods in which the composition described above are used and to uses of the composition in industrial processes.

In principle, a composition of the invention may be used in any process which requires the treatment of a material which comprises non-starch polysaccharide. Thus, a polypeptide or composition of the invention may be used in the treatment of non-starch polysaccharide material. Herein, non-starch polysaccharide material is a material which comprises or consists essential of one or, more typically, more than one non-starch polysaccharide.

Typically, plants and fungi and material derived therefrom comprise significant quantities of non-starch polysaccharide material. Accordingly, a polypeptide of the invention may be used in the treatment of a plant or fungal material or a material derived therefrom.

An important component of plant non-starch polysaccharide material is lignocellulose (also referred to herein as lignocellulolytic biomass). Lignocellulose is plant material that is composed of cellulose and hemicellulose and lignin. The carbohydrate polymers (cellulose and hemicelluloses) are tightly bound to the lignin by hydrogen and covalent bonds. Accordingly, a polypeptide of the invention may be used in the treatment of lignocellulolytic material. Herein, lignocellulolytic material is a material which comprises or consists essential of lignocellulose. Thus, in a method of the invention for the treatment of a non-starch polysaccharide, the non-starch polysaccharide may be a lignocellulosic material/biomass.

Accordingly, the invention provides a method of treating a non-starch polysaccharide in which the treatment comprises the degradation and/or modification of cellulose and/or hemicellulose.

Degradation in this context indicates that the treatment results in the generation of hydrolysis products of cellulose and/or hemicellulose and/or a pectic substance, i.e. saccharides of shorter length are present as result of the treatment than are present in a similar untreated non-starch polysaccharide. Thus, degradation in this context may result in the liberation of oligosaccharides and/or sugar monomers.

All plants and fungi contain non-starch polysaccharide as do virtually all plant- and fungal-derived polysaccharide materials. Accordingly, in a method of the invention for the treatment of a non-starch polysaccharide, said non-starch polysaccharide may be provided in the form of a plant or a plant derived material or a material comprising a plant or plant derived material, for example a plant pulp, a plant extract, a foodstuff or ingredient therefore, a fabric, a textile or an item of clothing.

The invention provides a method for producing a sugar from a lignocellosic material which method comprises contacting a composition as described herein with the lignocellulosic material.

Such a method allows free sugars (monomers) and/or oligosaccharides to be generated from lignocellulosic biomass. These methods involve converting lignocellulosic biomass to free sugars and small oligosaccharides with a polypeptide or composition of the invention.

The process of converting a complex carbohydrate such as lignocellulose into sugars preferably allows conversion into fermentable sugars. Such a process may be referred to as "saccharification." Accordingly, a method of the invention may result in the liberation of one or more hexose and/or pentose sugars, such as one or more of glucose, cellobiose, xylose, arabinose, galactose, galacturonic acid, glucuronic acid, mannose, rhamnose, sucrose and fructose.

Lignocellulolytic biomass suitable for use in the invention includes Biomass can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, switch grass, miscanthus, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof.

Apart from virgin biomass or feedstocks already processed in food and feed or paper and pulping industries, the biomass/feedstock may additionally be pretreated with heat, mechanical and/or chemical modification or any combination of such methods in order to enhance enzymatic degradation.

The fermentable sugars can be converted to useful value-added fermentation products, non-limiting examples of which include amino acids, vitamins, pharmaceuticals, animal feed supplements, specialty chemicals, chemical feedstocks, plastics, solvents, fuels, or other organic polymers, lactic acid, and ethanol, including fuel ethanol.

Specific value-added products that may be produced by the methods of the invention include, but not limited to, biofuels (including ethanol and butanol and a biogas); lactic acid; a plastic; a specialty chemical; an organic acid, including citric acid, succinic acid, fumaric acid, itaconic acid and maleic acid; 3-hydoxy-propionic acid, acrylic acid; acetic acid; 1,3-propane-diol; ethylene, glycerol; a solvent; an animal feed supplement; a pharmaceutical, such as a β-lactam antibiotic or a cephalosporin; vitamins; an amino acid, such as lysine, methionine, tryptophan, threonine, and aspartic acid; an industrial enzyme, such as a protease, a cellulase, an amylase, a glucanase, a lactase, a lipase, a lyase, an oxidoreductases, a transferase or a xylanase; and a chemical feedstock.

The composition, nature of substitution, and degree of branching of hemicellulose is very different in dicotyledonous plants (dicots, i.e., plant whose seeds have two cotyledons or seed leaves such as lima beans, peanuts, almonds, peas, kidney beans) as compared to monocotyledonous plants (monocots; i.e., plants having a single cotyledon or seed leaf such as corn, wheat, rice, grasses, barley). In dicots, hemicellulose is comprised mainly of xyloglucans that are 1,4-β-linked glucose chains with 1,6-β-linked xylosyl side chains. In monocots, including most grain crops, the principal components of hemicellulose are heteroxylans. These are primarily comprised of 1,4-β-linked xylose backbone polymers with 1,3-α linkages to arabinose, galactose, mannose and glucuronic acid or 4-O-methyl-glucuronic acid as well as xylose modified by ester-linked acetic acids. Also present are β glucans comprised of 1,3- and 1,4-β-linked glucosyl chains. In monocots, cellulose, heteroxylans and β-glucans may be present in roughly equal amounts, each comprising about 15-25% of the dry matter of cell walls. Also, different plants may comprise different amounts of, and different compositions of, pectic substances. For example, sugar beet contains about 19% pectin and about 21% arabinan on a dry weight basis.

Accordingly, a composition of the invention may be tailored in view of the particular feedstock which is to be used. That is to say, the spectrum of activities in a composition of the invention may vary depending on the feedstock in question.

Enzyme combinations or physical treatments can be administered concomitantly or sequentially. The enzymes can be produced either exogenously in microorganisms, yeasts, fungi, bacteria or plants, then isolated and added to the lignocellulosic feedstock. Alternatively, the enzymes are produced, but not isolated, and crude cell mass fermentation broth, or plant material (such as corn stover), and the like are added to the feedstock. Alternatively, the crude cell mass or enzyme production medium or plant material may be treated to prevent further microbial growth (for example, by heating or addition of antimicrobial agents), then added to the feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may serve as the lignocellulosic feedstock and be added into lignocellulosic feedstock.

In the method of the invention, a enzyme or combination of enzymes acts on a lignocellulosic substrate or plant biomass, serving as the feedstock, so as to convert this complex substrate to simple sugars and oligosaccharides for the production of ethanol or other useful fermentation products.

Accordingly, another aspect of the invention includes methods that utilize the composition described above together with further enzymes or physical treatments such as temperature and pH to convert the lignocellulosic plant biomass to sugars and oligosaccharides.

While the composition has been discussed as a single mixture it is recognized that the enzymes may be added sequentially where the temperature, pH, and other conditions may be altered to increase the activity of each individual enzyme. Alternatively, an optimum pH and temperature can be determined for the enzyme mixture.

The composition is reacted with substrate under any appropriate conditions. For example, enzymes can be incubated at about 25° C., about 30° C., about 35° C., about 37° C., about 40° C., about 45° C., about 50° C., about 55° C., about 60° C., about 65° C., about 70° C., about 75° C., about 80° C., about 85° C., about 90° C. or higher. That is, they can be incubated at a temperature of from about 20° C. to about 95° C., for example in buffers of low to medium ionic strength and/or from low to neutral pH. By "medium ionic strength" is intended that the buffer has an ion concentration of about 200 millimolar (mM) or less for any single ion component. The pH may range from about pH 2.5, about pH 3.0, about pH 3.5, about pH 4.0, about pH 4.5, about pH 5, about pH 5.5, about pH 6, about pH 6.5, about pH 7, about pH 7.5, about pH 8.0, to about pH 8.5. Generally, the pH range will be from about pH 3.0 to about pH 9.

Typically, the reaction may be carried out under low pH conditions as defined above. Thus, a method of the invention may be carried out such that no pH adjustment (i.e. to a more neutral pH is required). That is to say, an acid pretreated feedstock may be used as is with no requirement to addition of, for example, sodium hydroxide, prior to addition of a composition of the invention.

The feedstock may be washed prior to liquefaction/hydrolysis. Such washing may be with, for example, water.

Incubation of a composition under these conditions results in release or liberation of substantial amounts of the sugar from the lignocellulosic material. By substantial amount is intended at least about 20%, at least about 30%, at least about 40%, at least about 50%, at least about 60%, at least about 70%, at least about 80%, at least about 90%, at least about 95% or more of available sugar.

A liquefaction/hydrolysis or presaccharification step involving incubation with an enzyme or enzyme mixture can be utilized. This step can be performed at many different temperatures but it is preferred that the pretreatment occur at the temperature best suited to the enzyme mix being tested, or the predicted enzyme optimum of the enzymes to be tested. The temperature of the pretreatment may range from about 10° C. to about 80° C., about 20° C. to about 80° C., about 30° C. to about 70° C., about 40° C., to about 60° C., about 37° C. to about 50° C., preferably about 37° C. to about 80° C., more preferably about 50° C. In the absence of data on the temperature optimum, it is preferable to perform the pretreatment reactions at 37° C. first, then at a higher temperature such as 50° C. The pH of the pretreatment mixture may range from about 2.0 to about 10.0, but is preferably about 3.0 to about 5.0. Again, it may not be necessary to adjust the pH prior to saccharification since a composition for use in the invention is typically suitable for use at low pH as defined herein.

The liquefaction/hydrolysis or presaccharification step reaction may occur from several minutes to several hours, such as from about 1 hour to about 120 hours, preferably from about 2 hours to about 48 hours, more preferably from about 2 to about 24 hours, most preferably for from about 2 to about 6 hours. The cellulase treatment may occur from several minutes to several hours, such as from about 6 hours to about 168 hours, preferably about 12 hours to about 96 hours, more preferably about 24 hours to about 72 hours, even more preferably from about 24 hours to about 48 hours. These conditions are particularly suitable in case the liquefaction/hydrolysis or presaccharification step is conducted in a Separate Hydrolyis and Fermentation (SHF) mode.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 g/L-200 g/L, 40 g/L-200 g/L, 50 g/L-200 g/L, 60 g/L-200 g/L, 70 g/L-200 g/L, 80 g/L-200 g/L, 90 g/L, 80 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical mamimum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Sugars released from biomass can be converted to useful fermentation products such a one of those including, but not limited to, amino acids, vitamins, pharmaceuticals, animal feed supplements, specialty chemicals, chemical feedstocks, plastics, and ethanol, including fuel ethanol.

Significantly, a method of the invention may be carried out using high levels of dry matter (of the lignocellulosic material) in the hydrolysis reaction. Thus, the invention may be carried out with a dry matter content of about 5% or higher, about 8% or higher, about 10% or higher, about 11% or higher, about 12% or higher, about 13% or higher, about 14% or higher, about 15% or higher, about 20% or higher, about 25% or higher, about 30% or higher, about 35% or higher or about 40% or higher.

Accordingly, the invention provides a method for the preparation of a fermentation product, which method comprises:

a. degrading lignocellulose using a method as described herein; and b. fermenting the resulting material, thereby to prepare a fermentation product.

Such a process may be carried out without any requirement to adjust the pH during the process. That is to say, the process is one which may be carried out without the addition of any acid(s) or base(s). However, this excludes a pretreatment step, where acid may be added. The point is that the composition of the invention is capable of acting at low pH and, therefore, there is no need to adjust the pH of acid of an acid pretreated feedstock in order that saccharification may take place. Accordingly, a method of the invention may be a zero waste method using only organic products with no requirement for inorganic chemical input.

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including ethanol and butanol); lactic acid; 3-hydroxy-propionic acid; acrylic acid; acetic acid; 1,3-propanediol; ethylene; glycerol; a plastic; a specialty chemical; an organic acid, including citric acid, succinic acid and maleic acid; a solvent; an animal feed supplement; a pharmaceutical such as a β-lactam antibiotic or a cephalosporin; a vitamin; an amino acid, such as lysine, methionine, tryptophan, threonine, and aspartic acid; an enzyme, such as a protease, a cellulase, an amylase, a glucanase, a lactase, a lipase, a lyase, an oxidoreductase, a transferase or a xylanase; a chemical feedstock; or an animal feed supplement.

A method for the preparation of a fermentation product may optionally comprise recovery of the fermentation product.

Such a process may be carried out under aerobic or anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably about 5 or less, about 2.5 or less or about 1 mmol/L/h or less, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6 and even more preferably at least about 7 mmol/L/h.

The following Examples illustrate the invention:

Example 1

Saccharification of Corn Stover Hydrolysate Using Various Cellulases

Materials and Methods

The ability of three different cellulase preparations to saccharify a corn stover hydrolysate was evaluated. A *Talaromyces emersonii* enzyme product called Filtrase®NL (DSM Food Specialties, Delft, Netherlands) was compared with Laminex® BG and GC 220 (Genencor-Danisco, Rochester, USA). Laminex® BG and GC220 are considered to be the benchmark enzymes as presently available in the market.

Dilute acid pretreated corn stover prepared by NREL was used as the substrate for saccharification carried out with the cellulase preparations. The pretreated corn stover was stored at 4° C. The slurry was about 34% total solids with about 17% insoluble solids. The composition of the corn stover used for the pretreatment is set out in Table 1.

TABLE 1

The composition of the raw stover is as follows:

| component | % (w/w, dry basis) |
|---|---|
| cellulose | 33.9 ± 0.7 |
| xylan | 24.1 ± 1.1 |
| lignin | 11.4 ± 0.8 |
| extractives | 9.7 ± 0.3 |
| sucrose | 6.2 ± 1.0 |
| uronic acid[b] | 4.0 ± 0.2 |
| acetate | 3.9 ± 0.8 |
| arabinan | 3.1 ± 0.2 |
| non-structural inorganics | 2.0 ± 0.4 |
| protein | 1.6 ± 0.5 |
| galactan | 1.5 ± 0.1 |
| ash | 1.4 ± 0.5 |

[a]Mean ± standard deviation of 4 samples.
[b]Calculated value.

The dry matter concentration was verified and turned out to be 32.8% dry matter pulp (105° C., 48 hrs drying).

60 gr of the fiber was mixed with 120 gr water and pH (1.9) was adjusted to 5.0 using 4N NaOH and after that added up to 200 gr with water to obtain a 9.45% dry matter sludge. 10 gr portions of the sludge were divided into a 50 ml Schott-flask and each enzyme preparation was added at three different dosages (20, 61 and 204 µL respectively).

Subsequently the flasks were closed and incubated at 50° C. at 280 RPM for 140 hrs and sampled (3 ml) at 0, 21, 93 and 140 hrs, centrifuged using eppendorf centrifuge and the supernatant was decanted to a vial and analyzed for glucose, arabinose, xylose and galactose using NMR.

Results and Discussion

At the start of the incubation it was clear that the dilute acid pretreatment had done the work on the hemicellulose fraction since 24 g/L of xylose was present already from theoretical 30 g/L. The sugar composition at start of the saccharification is set out in Table 2; the free glucose concentration at time zero was around 4 g/L.

TABLE 2

Sugar composition at the start of the saccharification

| Raw material | Time (hrs) | Glu g/L | Gal g/L | Xyl g/L | Ara g/L | Acetic g/L | Lactic g/L | Total sugars |
|---|---|---|---|---|---|---|---|---|
| Sample 1 | 0 | 3.9 | 0.5 | 24.4 | 1.6 | 2.3 | 0.1 | 30.4 |
| Sample 2 | 0 | 3.9 | 0.5 | 23.9 | 1.5 | 2.3 | 0.1 | 29.8 |
| Average | 0 | 3.9 | 0.5 | 24.2 | 1.6 | 2.3 | 0.1 | 30.1 |

The pH was set at 5.0 at t=0 and was measured at 93 hrs and 140 hrs and was pH 4.5 in both cases, although the organic acid concentrations did not increase significantly. The drop in pH might have impacted the enzyme performance although the pH 4.5 is more ideal for application than pH 5.0 (due to lower bacterial contamination risk at 50° C.).

TABLE 3

Enzyme dosage of example 1 in mg enzyme protein (Bradford) per gram corn stover dry matter (mg EP/g CS dm), for low, medium and high enzyme dosage

| | Enzyme dosage mg EP/g CS dm | | |
|---|---|---|---|
| Enzyme | Low | Medium | High |
| GC220 | 1.0 | 3.1 | 10.4 |
| Filtrase ®NL | 0.15 | 0.47 | 1.5 |
| Laminex ® BG | 1.1 | 3.5 | 11.5 |

Figure 1B:
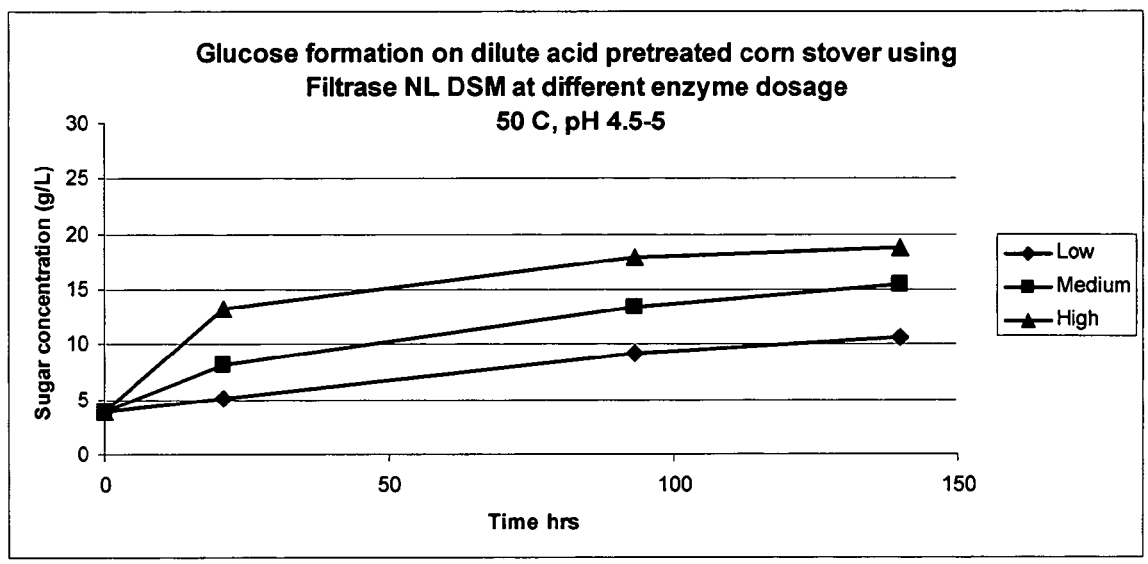
FIG. 1b=Filtrase® NL.
Figure 1C:
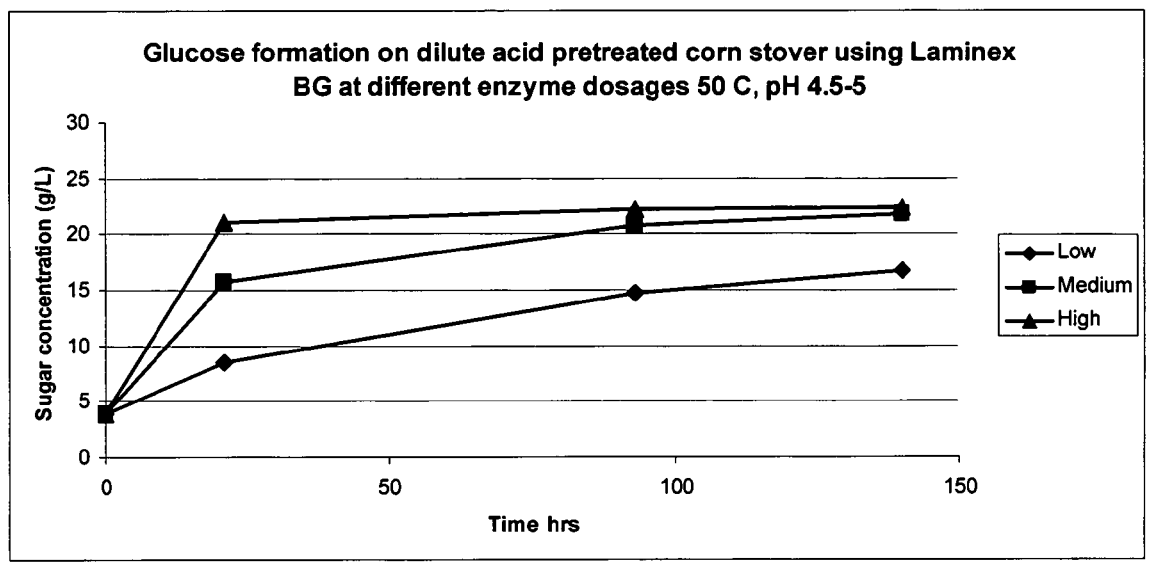
FIG. 1c=Laminex BG.
Figure 2A:
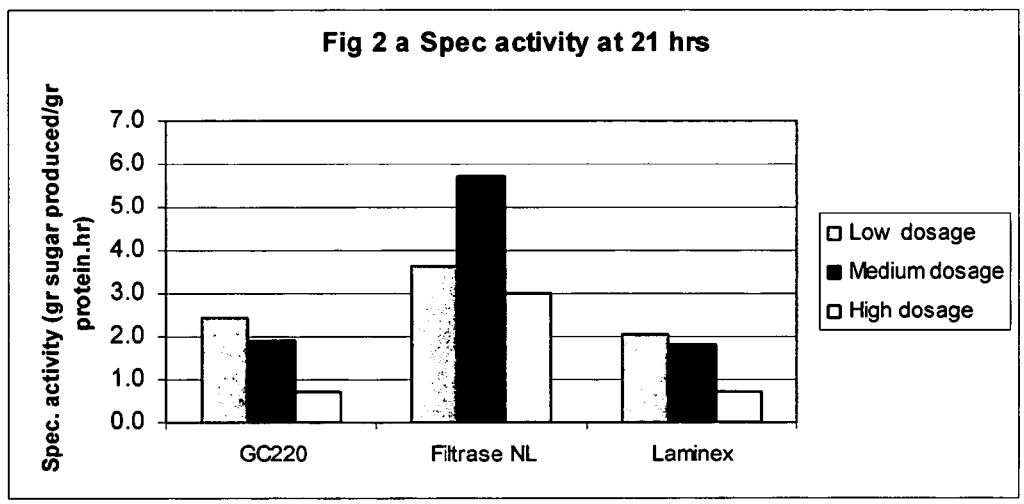
FIGS. 2a and 3a=specific activity at 21 hours.
Figure 2B:
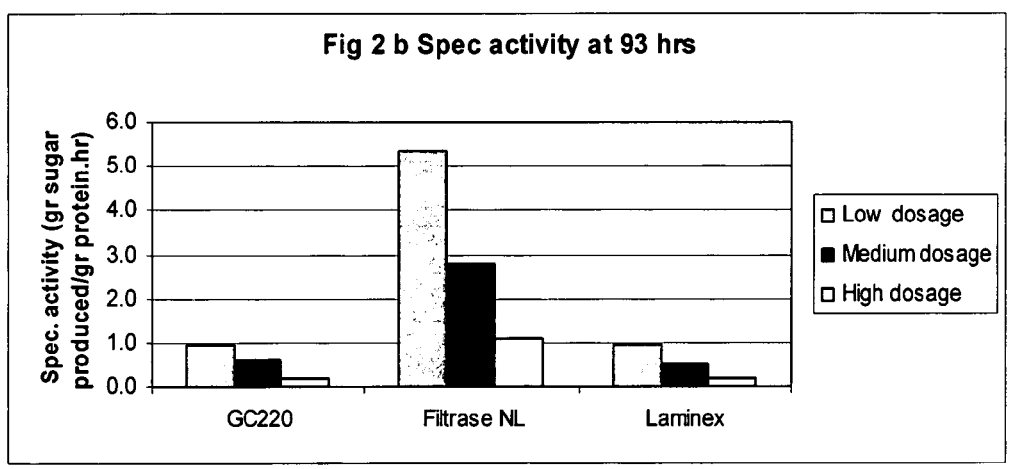
FIGS. 2b and 3b=specific activity at 93 hours.
Figure 2C:
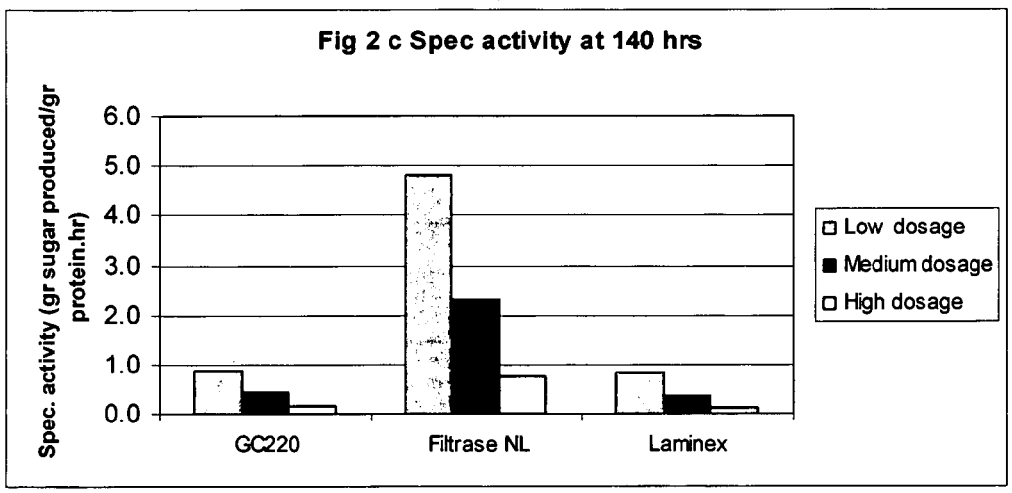
FIGS. 2c and 3c=specific activity at 140 hours.
Figure 3A:
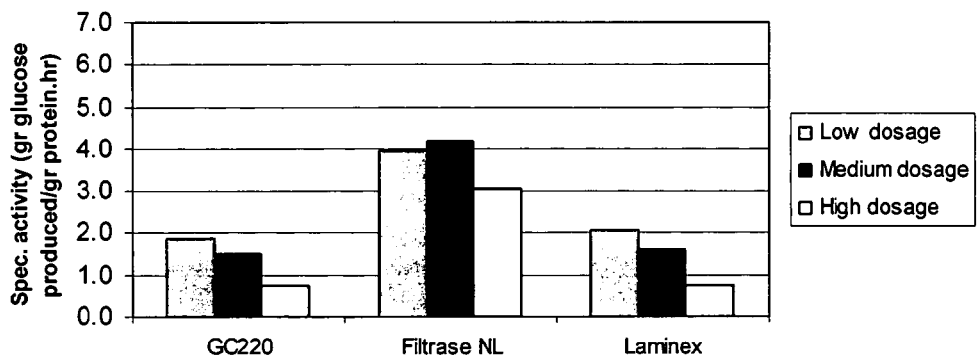
Figure 3B:
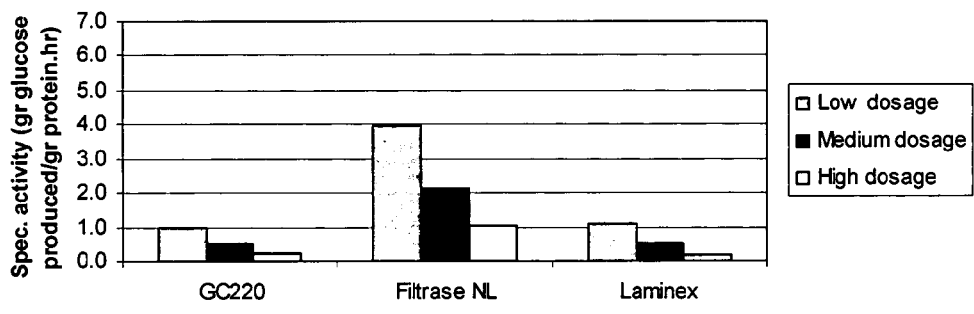
Figure 3C:
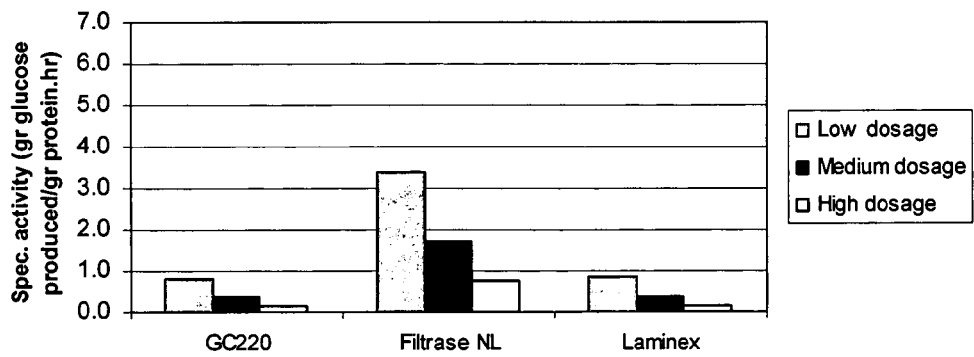

FIGS. 1a to c set out the saccharification results for the three enzyme preparations used in these experiments. From the data presented in FIGS. 1a to 1c it is clear that Laminex® BG very much resembles GC 220. However, the Talaromyces Filtrase®NL preparation seems to be very active since it liberates more sugars per amount of enzyme protein than GC 220 or Laminex® BG. Protein content of the enzyme mixtures was determined by Bradford protein assay and it was determined that the protein amount used in the experiments was less for the Talaromyces Filtrase®NL preparation than for GC 220 or Laminex® BG. See table 3. This demonstrates that the specific activity of the Talaromyces Filtrase®NL preparation is higher than the other cellulase preparations used in the comparison.

Specific Activity

The specific activity of the protein was calculated according to the following equation:

Productivity={[Glucose+arabinose+galactose+xylose] (gram monomeric sugars) at time X−[Glucose+arabinose+galactose+xylose](gram monomeric sugars) at time 0]}/[Overall incubation time (hrs)]/[protein amount in incubation (gr protein)]

in gr fermentable sugars/gr enzyme protein/hr.

Specific activity data were only calculated for experiments that produced more than 34 g/L of total sugar compared to the initially available 30 g/L of sugars at time 0 because small measurements errors have a high impact on the specific activities at low net production levels. The specific activity was checked for the 3 enzyme preparations at different time points and the results obtained are set out in FIGS. 2a to c and FIGS. 3a to 3c.

From the results obtained in these experiments, it is demonstrated that the Filtrase®NL enzyme preparation outperforms the other benchmark commercial enzyme preparations on sugar or glucose production per protein amount. GC 220 was comparable to Laminex® BG.

Example 2

Figure 4:
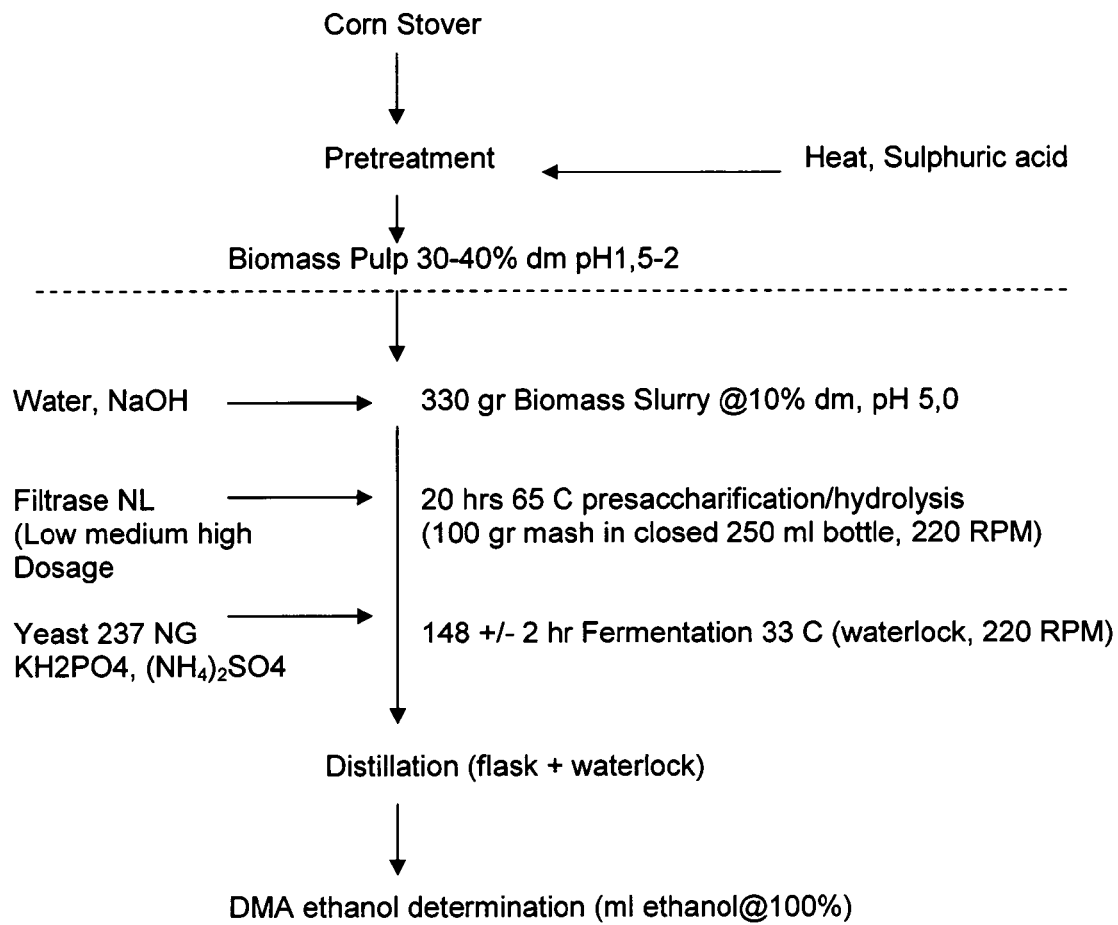
FIG. 4 shows a schematic for simultaneous saccharification and fermentation and distillation experiments.

SSF Experiments with Filtrase®NL and Saccharomyces cerevisiae 237NG Using Pretreated Corn Stover As follow up of the saccharification experiment described in Example 1, Simultaneous Saccharification and Fermentation and Distillation experiments for cellulose ethanol were carried out on 100 ml scale with dilute acid pretreated corn stover using Filtrase®NL and Yeast (Saccharomyces cerevisiae 237 NG). Using this technology, inhibitory glucose is removed and then higher hydrolysis yields are assumed to be obtained as compared to hydrolysis as such. A scheme for these experiments is set out in FIG. 4.

Materials and Methods

Ethanol yield per biomass dry weight input and hydrolysis yields were calculated as follows:

1. Dry matter input: dry weight determination 48 hrs, 105 C

2. Ethanol output: ml ethanol@100% measured on DMA
3. Glucan content: NREL sample we used data provided by NREL
4. Sugars in wash liquid were determined by NMR (sum of glucose, galactose, xylose and arabinose) and total sugars present in hydrolysate were calculated from the mass balance of the wash procedure (concentration of sugars multiplied by measured weight of of wash liquid)
5. Theoretical yield of ethanol from glucan was calculated by:
   a) Amount of fiber dry weight in 250 ml flask; exact (100.0+/−0.1 gr) weight of fiber slurry times dry matter content of starting material (gr fiber dm)*100/330 (we prepared 3 flasks of 100 gr mash each from a 330 gr fiber-slurry preparation after adjusting pH) value Around 10 gr fiber in 100 gr slurry=10% dm)
   b) Amount of glucan was calculated by multiplying glucan content as obtained from feedstock supplyers with dry matter content as we determined ourselves (3-4 gr glucan in unwashed case/100 gr fiberslurry and 5-6 gr glucan in washed fiiber preparations)
   c) Amount of potential glucose was calculated by multiplying glucan with 180/162 (chemical gain factor due to hydrolysis of glucan (glucan=cellulose=polymer of glucose)
   d) Amount of potential ethanol (assuming 0.79 gr ethanol/ml ethanol@100%) was calculated by multiplying amount of potential glucose with the theoretical maximum yield of ethanol on glucose being 0.511 gr ethanol/gr glucose and assuming a fermentation yield of 91.5% of the theoretical maximum (industrial average is assumed to be 91.5%+/−1.5% (this means between 90% and 93%).
   e) (Cellulose or glucan) Hydrolysis %=100*amount of ethanol produced (gr)/theoretical maximum ethanol (gr)

Results & Discussion

When using different enzyme dosages, low medium and high enzyme (1, 2 and 3 respectively) dosage increasing amounts of ethanol were obtained.

Figure 5:
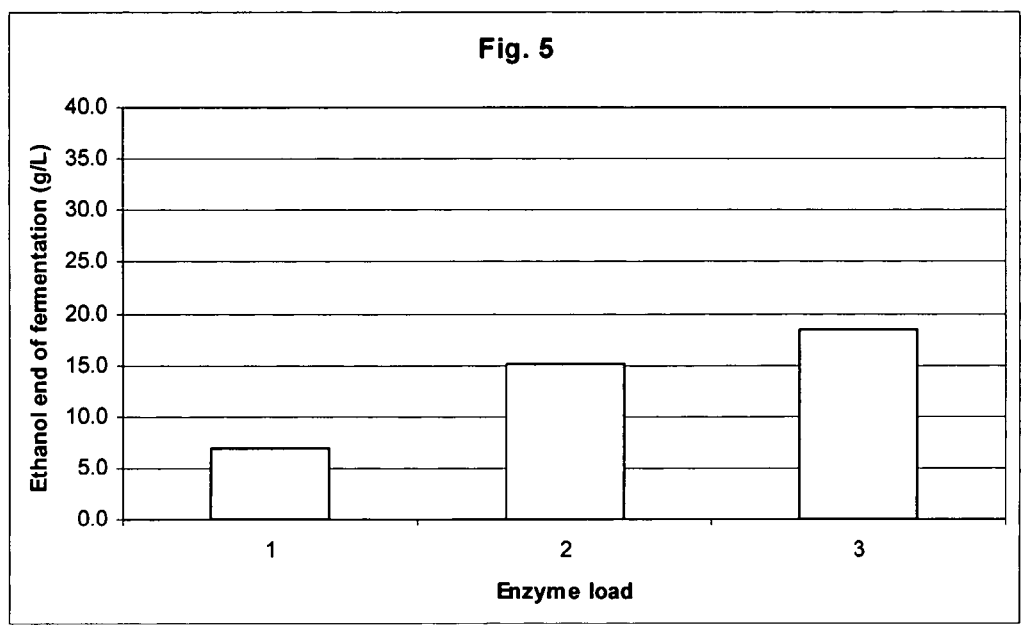
FIG. 5 shows ethanol production from dilute acid pretreated corn stover in simultaneous saccharification and fermentation and distillation experiments using Filtrase®NL.
Figure 6:
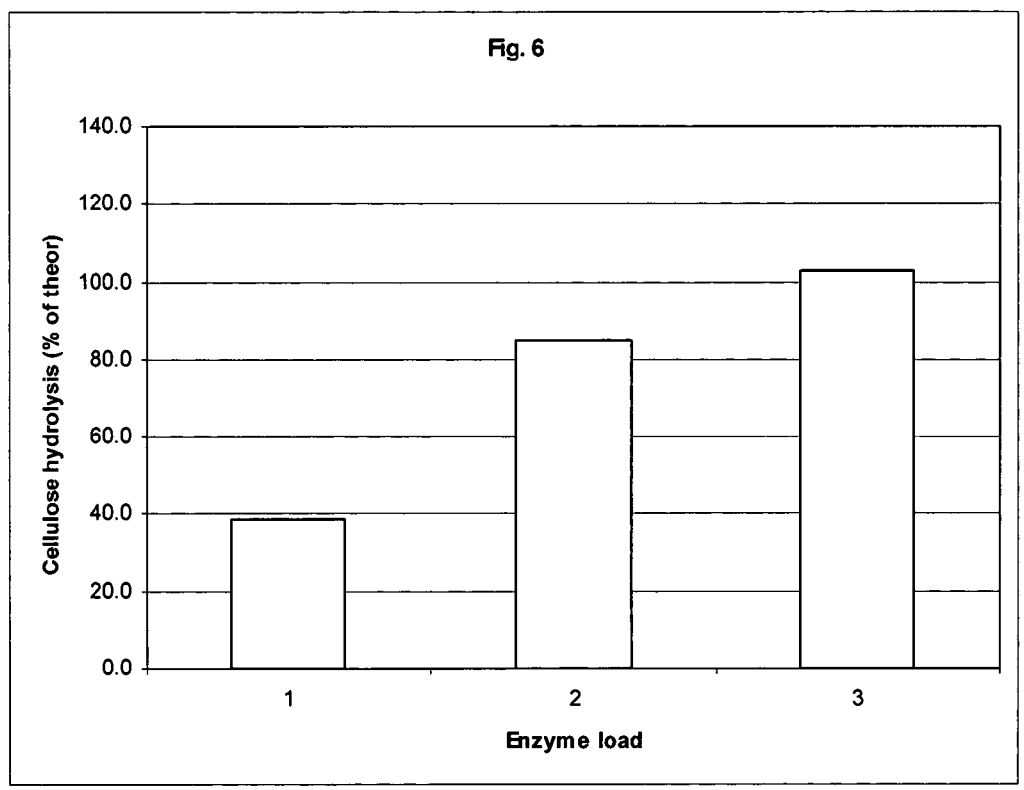
FIG. 6 shows the hydrolysis yield from dilute acid pretreated corn stover in simultaneous saccharification and fermentation and distillation experiments using Filtrase®NL.

The theoretical maximum amount of ethanol that could have been produced at 10.2% dry matter and 34% glucan content (NREL-analysis) would have been 102*0.34*180/162*0.91*0.511=17.9 g ethanol/L medium. As shown in FIGS. 5 and 6 it can be seen that this amount of ethanol was reached at the highest enzyme dosage demonstrating that full saccharification is possible with Filtrase®NL. Surprisingly, this thermophilic enzyme is also very effective at a mesophilic temperature of 33° C.

Example 3

Saccharification of Wheat Straw Using Filtrase®NL

Wheat straw was pretreated with steam at 195° C. for 12 minutes as described by Jan Larsen et al. Chem. Eng. Technol. 2008, 31, No. 5, 1-9. The fiber was hydrolysed using Filtrase®NL at 8% dry matter without any addition of acid or base at pH 3.8 at 60° C. while shaking at 175 RPM in a shaker incubator.

Figure 7:
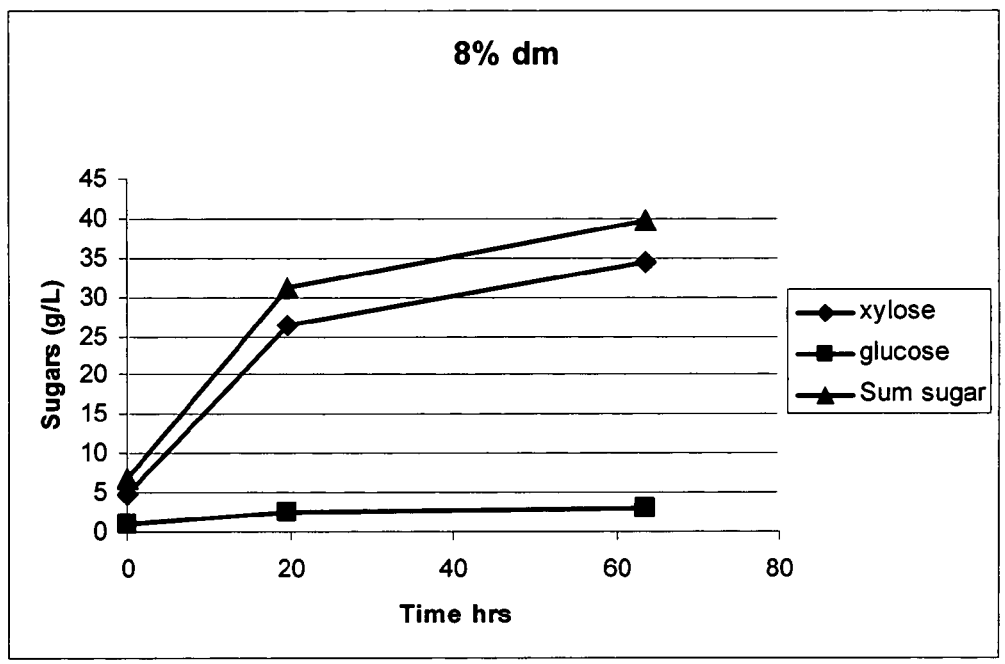
FIG. 7 shows sugar formation from wheat straw pretreated with steam, at 60° C., pH 3.8 using Filtrase®NL.

At a 50% glucan content in the fiber, one would expect maximum 40 g/L of glucose to be produced in this experiment the hydrolysis yield is >85% and the total ethanol potential of this hydrolysate would be 19 g/L at 92% fermentation yield on total sugars of 40 g/L. FIG. 7 sets out the results of this experiment, demonstrating that this level of glucose was achieved. Thus, the acidic properties of the enzyme preparation thus enables ethanol production without any addition of acid or base as pH 3.8 is also optimal for the Yeast *Saccharomyces cerevisiae*.

Example 4

Saccharification of Wheat Straw Using Filtrase®NL

In 10 L scale pretreated wheat straw feedstock at 33-34% dry matter as used in example 3 were mixed with water an enzyme solution obtained from Filtrase®NL by dialyzing away glycerol (which is present in the commercial product as a formulation agent) with water over a 10 kD dialfiltration UF-unit from the commercial preparation and concentrating the enzyme 10 fold. The total dry matter concentration in the preparation after 6 hrs is 28% wheat straw dry matter. See Table 4.

TABLE 4

Saccharification of feedstock pretreated wheatstraw in fed-batch operation, overview of dosages at t = 1 h, t = 3 h and t = 6 h. at high enzyme dosage (High) and medium enzyme dosage (Medium).

Figure 8:
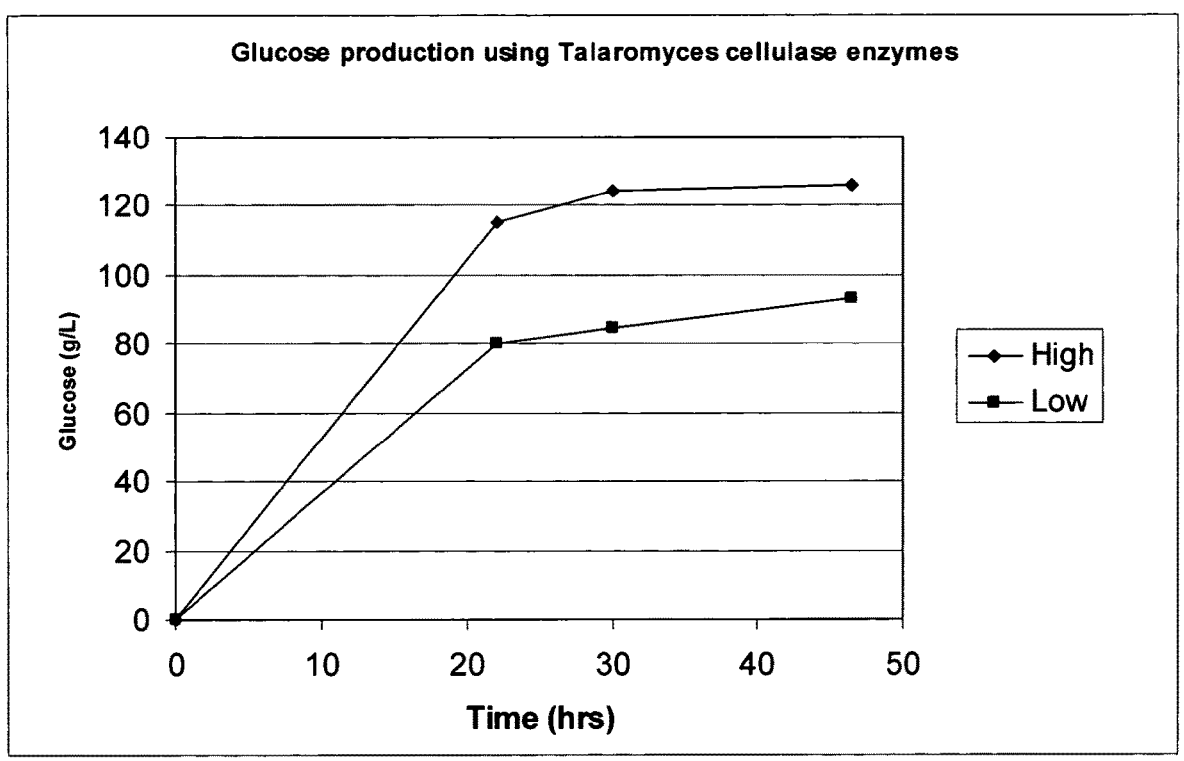
FIG. 8 shows glucose production using *Talaromyces* cellulases

| Age (h) | Compound | High | Medium |
|---|---|---|---|
| 0.00 | Feedstock | 1000 g | 1000 g |
|  | Cellulase enzyme | 116 g | 47 g |
|  | Water | 154 g | 227 g |
| 3.00 | Feedstock | 1600 g | 1600 g |
|  | Cellulase enzyme | 36 g | 14 g |
|  | Water | 545 g | 567 g |
| 6.00 | Feedstock | 3436 g | 3436 g | pH was controlled at 5.0 +/− 0.2 using 8N KOH and 4N $H_2SO_4$
Temperature was controlled between 55 and 60° C.
Stirring was done at 700 RPM using 1 standard Rushton turbine After one day already very high glucose concentrations could be measured of >110 g/L and after two days of incubation, a glucose concentration of 128 g/L was measured using NMR sugar measurement in the supernatant after removing of the remaining lignin solids by means of centrifugation showing that the enzyme is less severe inhibited by glucose than expected from literature. See FIG. 8.

This glucose concentration is the highest glucose concentration ever observed with a *Talaromyces* cellulose preparation which enables also commercial SHF processes using this enzyme while achieving a theoretical maximum of 65 g/L of ethanol when all glucose would be converted to ethanol (=0.511*128 g/L).

Theoretical Maximum Yield

The theoretical maximum yield (Yps max in gr product per gram glucose) of a fermentation were calculated as follows. For ethanol, 1 mole of glucose (180 gr) yields according to normal glycolysis fermentation pathway in yeast 2 moles of ethanol (=2×46=92 gr ethanol. The theoretical maximum yield of ethanol on glucose is therefore 92/180=0.511 gr ethanol/gr glucose.

For Butanol (MW 74 gr/mole) or iso butanol, the theoretical maximum yield is 1 mole of butanol per mole of glucose. So Yps max for (iso-)butanol=74/180=0.411 gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

TABLE 5

Achievable glucose concentrations in SHF and achievable product concentrations in SSF for products with different Yps max (g/g).

| SHF | | SSF Yps max (g/g) | | |
|---|---|---|---|---|
| | | 0.511 | 0.411 | 1 |
| | | | Glucose | |
| | Achievable concentration g/L | Ethanol g/L | butanol g/L | lactic acid g/L |
| Minimum | 25 | 12.8 | 10.3 | 25.0 |
| Maximum | 250 | 127.8 | 102.8 | 250.0 |

No Glucose Inhibition:

Table 6 shows a kinetic comparison of beta glucosidases. It is clear from that table that the Ki (glucose) of *Talaromyces* betaglucosidase is very low (0.045), which shows that the composition according to the invention is not glucose repressed.

TABLE 6

Kinetic comparison of beta glucosidases from different sources:

| | Talaromyces | Trichoderma | A. niger | A. oryzae | Unit |
|---|---|---|---|---|---|
| Vmax (cellobiose) | 1080 | 470 | 400 | 10131 | gr/gr protein/hr |
| Km (cellobiose) | 0.02 | 0.68 | 0.05 | 2.39 | g/L |
| Ki (glucose) | 0.045 | 0.108 | 3 | 245 | g/L |
| S (Cellobiose) | 2.5 | 2.5 | 2.5 | 2.5 | g/L |

The invention claimed is:

1. A method for the treatment of corn stover which method comprises contacting pretreated corn stover with a composition comprising three or more enzyme activities, said enzyme activities being cellulase and/or hemicellulase activities, wherein:
   a) the composition comprises an endoglucanase, cellobiohydrolase and β-glucosidase which are derived from *Talaromyces emersonii* and the composition is provided in an amount from 0.15 to 1.5 mg enzyme protein per gram corn stover dry matter (mg EP/g CS dm)
   b) the pH during the treatment is about 4.5 or lower,
   c) the pretreated corn stover is produced by a method comprising exposing corn stover to an acid prior to contacting the corn stover with the composition,
   d) the treatment is carried out at a dry matter content of 15% to 25%; and
   e) said method results in at least 80% conversion of cellulose to a sugar or sugars.

2. The method according to claim 1, wherein the pH during the treatment is 4.0 or lower.

3. The method according to claim 1, wherein the enzyme activities are thermostable.

4. The method according to claim 1, wherein the enzyme activities are capable of acting at low pH.

5. The method according to claim 1, wherein the composition comprises endo-1,3(1,4)-β glucanase activity and endo-β-1,4-glucanase activity, both of which activities are derived from *Talaromyces emersonii*.

6. The method according to claim 4 wherein the composition comprises one or more xylanase activities.

7. The method according to claim 1, wherein the composition comprises one or more of the following proteins: an expansin, an expansin-like protein, a cellulose induced protein, a cellulose integrating protein, a scaffoldin or a scaffoldin-like protein, wherein said one or more proteins are optionally derived from *Talaromyces emersonii*.

8. The method according to claim 1, wherein the treatment comprises the degradation of cellulose and/or hemicellulose.

9. A method for producing a sugar or sugars from corn stover which method comprises contacting the pretreated corn stover as defined in claim 1 with the composition as defined in claim 1.

10. The method according to claim 9, wherein the sugars are monomeric and/or multimeric sugars.

11. The method according to claim 9, wherein at least one of the sugars produced is a fermentable sugar.

12. The method according to claim 11, wherein at least one of the sugars produced is glucose, cellobiose, xylose, arabinose, galactose, galacturonic acid, glucuronic acid, mannose, rhamnose, sucrose or fructose.

13. The method according to claim 1, wherein the pretreatment further comprises exposing the corn stover to a solvent, heat, a peroxide, ozone, mechanical shredding, grinding, milling or rapid depressurization, or a combination of any two or more thereof.

14. A method for producing a fermentation product, which method comprises:
   producing a fermentable sugar using the method according to claim 1; and
   fermenting the resulting fermentable sugar, thereby to produce a fermentation product.

15. The method according to claim 14, wherein the fermentation product is ethanol, butanol, lactic acid, a plastic, an organic acid, a solvent, an animal feed supplement, a pharmaceutical, a vitamin, an amino acid, an enzyme or a chemical feedstock.

16. The method according to claim 1, wherein the composition comprises one or more of the following proteins: an expansin, an expansin-like protein, a cellulose induced protein, a scaffoldin or a scaffoldin-like protein, wherein said one or more proteins are optionally derived from *Talaromyces emersonii*.

17. The method of claim 1, wherein said composition is provided at about 0.15 mg enzyme protein per gram corn stover dry matter (mg EP/g CS dm).

18. The method of claim 1, wherein said composition is provided at about 0.5 mg enzyme protein per gram corn stover dry matter (mg EP/g CS dm).

19. The method of claim 1, wherein said composition is provided at 1.5 mg enzyme protein per gram corn stover dry matter (mg EP/g CS dm).

* * * * *